(12) United States Patent
Yao et al.

(10) Patent No.: US 7,417,168 B2
(45) Date of Patent: Aug. 26, 2008

(54) METHOD FOR PREPARING HYDROXYLAMINE

(75) Inventors: Pin-To Yao, Taipei (TW); Cheng-Fa Hsieh, Taipei (TW); Yuh-Ing Hwang, Taipei (TW)

(73) Assignee: China Petrochemical Development Corporation, Taipei (TW)

( * ) Notice: Subject to any disclaimer, the term of this patent is extended or adjusted under 35 U.S.C. 154(b) by 0 days.

(21) Appl. No.: 11/732,837

(22) Filed: Apr. 5, 2007

(65) Prior Publication Data

US 2008/0015388 A1 Jan. 17, 2008

(30) Foreign Application Priority Data

Apr. 7, 2006 (TW) ................ 95112427 A

(51) Int. Cl.
*C07C 239/08* (2006.01)
(52) U.S. Cl. ...................... 564/300; 564/301
(58) Field of Classification Search ............. 564/300, 564/301
See application file for complete search history.

(56) References Cited

U.S. PATENT DOCUMENTS 3,767,758 A 10/1973 Mars et al.
4,062,927 A 12/1977 De Rooij et al.

*Primary Examiner*—Brian J Davis
(74) *Attorney, Agent, or Firm*—Edward Angell Palmer & Dodge LLP; Peter F. Corless; Dwight D. Kim

(57) ABSTRACT

A method for preparing hydroxylamine is provided that includes the steps of (i) pretreating an acidic buffer solution; and (ii) reducing nitrate ions in the acidic buffer solution with hydrogen to give hydroxylamine in the presence of catalysts, wherein the pretreatment is performed by adding a precipitant represented by formula (I) to the acidic buffer solution, $$[(A)_a M(CN)_6 \cdot x H_2 O] \qquad (I)$$

allowing the metal impurities in the acidic buffer solution to react with the precipitant to form metal complex, and then to remove the metal complex. The metal complex is formed and separated by pretreating the acidic buffer solution with a specific precipitant without adjusting pH and changing the composition of the acidic buffer solution prior to hydroxylamine synthesis, thus enhancing the selectivity of the hydroxylamine production.

9 Claims, No Drawings

METHOD FOR PREPARING HYDROXYLAMINE

FIELD OF THE INVENTION

The present invention relates to a method for preparing hydroxylamine, and more particularly, to a method for preparing hydroxylamine by reduction of nitrate ions with hydrogen.

BACKGROUND OF THE INVENTION

Industrial preparation of hyroxylamine is usually carried out under a recycling system by combining with other processes, for example, the hydroxylamine-oxime reaction system. In this system, nitric acid and hydrogen are used as starting material, and phosphate salt is used as an inorganic processing solution. Nitrate ions are reduced to hydroxylamine in the presence of catalysts. The hydroxylamine obtained is subjected to a condensation reaction with cyclohexanone to give cyclohexanone oxime. After oxime is produced, nitric acid is added to the phosphate processing solution or nitrous gases is introduced and absorbed to form nitric acid, so as to increase the required amount of nitrate ions. Thereafter, the phosphate inorganic processing solution is introduced to a hydroxylamine reactor to generate hydroxylamine. These reactions are shown as follows:

Preparation of Hydroxylammonium Phosphate by the Reduction of Nitrate Ions $$NH_4NO_3 + 2H_3PO_4 + 3H_2 \rightarrow NH_3OH \cdot H_2PO_4 + NH_4H_2PO_4 + 2H_2O$$

Preparation of Cyclohexanone Oxime by Condensation with Cyclohexanone $$NH_3OH \cdot H_2PO_4 + C_6H_{10}O \rightarrow C_6H_{10}NOH + H_2O + H_3PO_4$$

Supplement of Nitrate Ions into the Phosphate Inorganic Processing Solution $$HNO_3 + H_2PO_4^- \rightarrow NO_3^- + H_3PO_4$$

Since the inorganic processing solution containing phosphate salt is recycled during the processing, the quality of the obtained hydroxylamine is directly affected by the quality of the inorganic processing solution. In the inorganic processing solution, phosphoric acid and phosphate salts are used as an acidic buffer solution. The metal impurities formed through the corrosion of apparatuses or other causes will be dissolved in the acidic buffer solution during the recycling processing and will decrease the selectivity of hydroxylamine production.

To illustrate, U.S. Pat. No. 3,767,758 describes that an inorganic processing solution containing molybdenum, rhodium or ruthenium causes a decrease of the selectivity of hydroxylamine production. Further, U.S. Pat. No. 4,062,927 discloses that when hydroxylamine is prepared by reduction of nitrate ions or nitrogen monoxide with hydrogen in an acidic solution, the acidic solution can corrode apparatuses or facilities, and thus causes the contamination with heavy metal. Among the heavy metal contaminants, molybdenum contaminants can cause 5~15% decrease of the selectivity of hydroxylamine production. Therefore, the molybdenum contaminants are removed from the acidic solution by coprecipitation of the molybdenum contaminants together with the ion-ammonium phosphate precipitate.

However, the coprecipitation requires a pH of over 3.5 to give precipitates, and a basic solution is required to adjust the pH of the acidic inorganic processing solution used in the hydroxylamine-oxime recycling system. However, this treatment will increase the cost and the complexity of processes, and the selectivity of the hydroxylamine production is only promoted up to 83%.

Therefore, it is desired to provide a simple process with high selectivity for the preparation hydroxylamine.

SUMMARY OF THE INVENTION

To overcome the above-mentioned problems of the prior art, it is an object of this invention to provide a method for preparing hydroxylamine with a high selectivity of hydroxylamine production.

Another object of this invention is to provide a method for preparing hydroxylamine, wherein the metal impurities can be removed without adjusting pH of the acidic buffer solution.

A further object of this invention is to provide a method for preparing hydroxylamine, wherein the metal impurities can be removed without changing the composition of the acidic buffer solution.

To achieve the aforementioned and other objects, a method for preparing hydroxylamine according to the present invention is provided, which comprises the steps of: (i) pretreating an acidic buffer solution composing of an acidic buffer reagent, nitric acid or nitrates, and metal impurities by adding a precipitant represented by formula (I), $$[(A)aM(CN)_6 \cdot xH_2O] \qquad (I),$$

whichin, each symbol is defined as below, followed by removing the metal complex formed by the reaction of the precipitant with the metal impurities in the acidic buffer solution; and (ii) reducing nitrate ions provided by the nitric acid and nitrates in the acidic buffer solution with hydrogen in the presence of catalysts to give hydroxylamine. According to the present invention, the acidic buffer solution is pretreated with a specific precipitant without adjusting pH of the acidic buffer solution, and the formed metal complex can be easily removed. Because the acidic buffer solution used in the hydroxylamine preparation is pretreated to remove metal impurities before hydroxylamine synthesis, the selectivity of the hydroxylamine production can be significantly enhanced.

DETAILED DESCRIPTION OF THE PREFERRED EMBODIMENTS

The following embodiments are provided to illustrate the disclosures of the present invention. These and other advantages and effects of the present invention can be apparently understood by those skilled in the art after reading this specification. The present invention can also be performed or applied by other different embodiments. The details of the specification may be modified and varied on the basis of different points and applications without departing from the spirit of the present invention.

In the present invention, nitrate ions in a pretreated acidic buffer solution are reduced to hydroxylamine with hydrogen in the presence of catalysts. The acidic buffer solution includes an acidic buffer reagent, nitric acid or nitrates, and metal impurities. Examples of the acidic buffer reagent include, such as sulfuric acid, phosphoric acid, and salts thereof.

In one embodiment of the present invention, the phosphate inorganic processing solution in hydroxylamine-oxime recycling system is used as the acidic buffer solution for synthesizing hydroxylammonium phosphate. The acidic buffer solution comprises phosphate irons, ammonium ions, nitrate ions, and metal impurities, such as ion, molybdenum, nickel, bismuth, cobalt, copper, manganese, tin, tungsten, zinc, and the like. Since the metal impurities in the acidic buffer solution will result in decreasing selectivity for hydroxylamine production, a pretreatment is needed to be performed in order to remove the metal impurities. As used herein, the selectivity of the hydroxylamine production is defined as followed:

The selectivity for hydroxylamine production=two times the yield of hydroxylamine/the consumption of hydrogen ions×100%.

In the present invention, the pretreatment includes: (a) adding a precipitant represented by formula (I) below to the acidic buffer solution; (b) reacting the precipitant with the metal in the acidic buffer solution to form metal complex, and (c) removing the metal complex from the acidic buffer solution,

[(A) aM(CN)$_6$·xH$_2$O]    (I),

Wherein A is selected from the group consisting of IA metals and NH$_4$, M is IIIB metals, a is an integer of 3 or 4, and x is an integer of 0 to 10. Preferably, M is iron, a is 4, and x is 0. The preferred examples include, but not limited to, yellow prussiates [Na$_4$Fe(CN)$_6$, K$_4$Fe(CN)$_6$, (NH$_4$)$_4$Fe(CN)$_6$].

In one embodiment of the present invention, the added amount of the precipitant represented by formula (I), based on the weight of the whole acidic buffer solution, is in the range between 0.001 and 0.12 wt %, and preferably in the range between 0.01 and 0.08 wt %. The added amount of the precipitant in step (a) of the pretreatment is not limited thereto, and to those skilled in the art, the added amount of the precipitant can be adjusted according to the content of the metals in the acidic buffer solution.

In the present invention, step (b) of the pretreatment may use a proper method to mix the precipitant with the acidic buffer solution completely, and to react with metals in the acidic buffer solution to form metal complex. Mixing method includes, but not limited to, stirring, circular convection, and the like. If mix by stirring is applied, it is usually mixed for 1 to 5 hours, and preferably 2 to 4 hours, but it is not limited thereto. The temperature for forming metal complex is controlled in the range between crystallization point and 130° C., preferably between 25° C. and 120° C., and more preferably between 40° C. and 95° C. Then, it is followed by step (c) of the pretreatment. In this embodiment, the metal complex is separated from the acidic buffer solution by filtration after precipitation occurred. The pretreatment can be carried out at a pH less than 3.5, or it can be performed directly at a pH between 0.5 and 1.8. Because the pretreatment can be carried out directly without adjusting the pH of the acidic buffer solution in the present invent, metal impurities in the acidic buffer solution can be removed by forming metal complex without an additional step for neutralization In this embodiment, the phosphate inorganic processing solution in the hydroxylamine-oxime recycling system is used as the acidic buffer solution for synthesizing hydroxylammoniun phosphate. Accordingly, the pretreated acidic buffer solution may be charged with nitrate ions before hydroxylamine is synthesized. Preferably, the amount of nitrate ions in the acidic buffer solution, based on the weight of the whole acidic buffer solution, is adjusted to 13 to 18 wt %, and more preferably adjusted to 14 to 16.5 wt %.

In the present invention, the condition for synthesizing hydroxylamine is not specially restricted, and those conditions for reducing nitrate ions with hydrogen are all suitable.

For example, reaction temperature may be 20° C. to 100° C., preferably 30° C. to 90° C., and more preferably 40° C. to 65° C.; reaction pressure may be 10 to 30 kg/cm$^2$, preferably 18 to 26 kg/cm$^2$, and more preferably 18 to 24 kg/cm$^2$; and the reaction may be conducted at a pH between 0.5 and 6, and preferably between 1 and 3.5. As to the composition of inletting gas used for synthesizing hydroxylamine, hydrogen is usually between 30 to 70% by volume, based on the volume of whole hydrogen and nitrogen, and more preferably between 45 to 55% by volume Examples of catalysts used in the hydroxylamine synthesis include, but not limited to, noble metal catalysts including palladium and palladium-platinium catalysts. Examples of carriers of the catalysts include, but not limited to, carbon and aluminum oxide. Content of the noble metal catalysts is usually, based on weight of the whole carriers and catalysts, between 1 and 25 wt %, preferably between 5 and 15 wt %. Content of catalysts used for hydroxylamine synthesis is usually, based on weight of the whole acidic buffer solution, between 0.2 and 5 wt %.

In the present invention, a pretreated acidic buffer solution is used for hydroxylamine synthesis. Because the metal impurities, especially nickel and iron, can be efficiently removed from the acidic buffer solution by pretreating the acidic buffer solution without adjusting pH, the selectivity for the hydroxylamine production can be significantly enhanced over 85%, even over 90% or over 94%.

EXAMPLES

Example 1

A phosphate inorganic processing solution in a hydroxylamine-oxime recycling system was used as an acidic buffer solution for preparing hydroxylammonium phosphate. The composition of the phosphate inorganic solution was analyzed by titration. The results are shown in table 1.

Then, 0.012 wt % yellow prussiate of potassium [K$_4$Fe(CN)$_6$] was added to the phosphate inorganic processing solution and stirred at 40° C. to form precipitate. The precipitate was filtered off, and a pretreated acidic buffer solution was obtained. The composition of the pretreated phosphate inorganic processing solution was analyzed by titration. The results are shown in table 1.

TABLE 1

| | pH | H$^+$ | H$_2$PO$_4^-$ | NH$_4^+$ | NH$_3$OH$^+$ | NO$_3^-$ |
|---|---|---|---|---|---|---|
| Composition of inorganic processing solution before pretreatment (wt %) | 1.8 | 0.162 | 22.36 | 5.12 | 0.106 | 10.52 |
| Composition of inorganic processing solution after pretreatment (wt %) | 1.8 | 0.162 | 22.36 | 5.13 | 0.106 | 10.52 |

Next, a step of allowing the pretreated phosphate inorganic processing solution to absorb nitric acid was carried out. After which, the composition of the phosphate inorganic solution was analyzed by titration. The results are shown in Table 2.

Thereafter, hydrogen and nitrogen were introduced into the phosphate inorganic processing solution at 50° C. under a pressure of 24 kg/cm$^2$ in the presence of catalysts. Hydroxylammonium phosphate was obtained. The selectivity for reducing nitrate ions to give hydroxylamine is 85.21%.

TABLE 2

|  | $H^+$ | $H_2PO_4^-$ | $NH_4^+$ | $NH_3OH^+$ | $NO_3^-$ |
|---|---|---|---|---|---|
| Composition of inorganic processing solution after absorbing nitric acid (wt %) | 0.290 | 20.11 | 4.17 | 0.079 | 14.34 |
| Selectivity for hydroxylamine production |  |  | 85.21% |  |  |

Example 2

A phosphate inorganic processing solution in a hydroxylamine-oxime recycling system was used as an acidic buffer solution for preparing hydroxylammonium phosphate. The composition of the phosphate inorganic solution was analyzed by titration. The results are shown in table 3.

Then, 0.035 wt % yellow prussiate of potassium [$K_4Fe(CN)_6$] was added to the phosphate inorganic processing solution and stirred at 50° C. to form precipitate. The precipitate was filtered off, and a pretreated acidic buffer solution was obtained. The composition of the pretreated phosphate inorganic processing solution was analyzed by titration. The results are shown in table 3.

TABLE 3

|  | pH | $H^+$ | $H_2PO_4^-$ | $NH_4^+$ | $NH_3OH^+$ | $NO_3^-$ |
|---|---|---|---|---|---|---|
| Composition of inorganic processing solution before pretreatment (wt %) | 1.8 | 0.168 | 22.56 | 5.13 | 0.108 | 10.43 |
| Composition of inorganic processing solution after pretreatment (wt %) | 1.8 | 0.167 | 22.57 | 5.13 | 0.108 | 10.43 |

Next, a step of allowing the pretreated phosphate inorganic processing solution to absorb nitric acid was performed. After which, the composition of the phosphate inorganic solution was analyzed by titration. The results are shown in Table 4.

Thereafter, hydrogen and nitrogen were introduced into the phosphate inorganic processing solution at 50° C. under a pressure of 24 kg/cm² in the presence of catalysts. Hydroxylammonium phosphate was obtained. The selectivity for reducing nitrate ions to give hydroxylamine is 86.80%.

TABLE 4

|  | $H^+$ | $H_2PO_4^-$ | $NH_4^+$ | $NH_3OH^+$ | $NO_3^-$ |
|---|---|---|---|---|---|
| Composition of inorganic processing solution after absorbing nitric acid (wt %) | 0.293 | 20.13 | 4.15 | 0.074 | 15.2 |
| Selectivity for hydroxylamine production |  |  | 86.80% |  |  |

Example 3

A phosphate inorganic processing solution in a hydroxylamine-oxime recycling system was used as an acidic buffer solution for preparing hydroxylammonium phosphate. The composition of the phosphate inorganic solution was analyzed by titration. The results are shown in table 5.

Then, 0.054 wt % yellow prussiate of potassium [$K_4Fe(CN)_6$] was added to the phosphate inorganic processing solution and stirred at 70° C. to form precipitate. The precipitate was filtered off, and a pretreated acidic buffer solution was obtained. The composition of the pretreated phosphate inorganic processing solution was analyzed by titration. The results are shown in table 5.

TABLE 5

|  | pH | $H^+$ | $H_2PO_4^-$ | $NH_4^+$ | $NH_3OH^+$ | $NO_3^-$ |
|---|---|---|---|---|---|---|
| Composition of inorganic processing solution before pretreatment (wt %) | 1.8 | 0.164 | 22.39 | 5.18 | 0.107 | 10.57 |
| Composition of inorganic processing solution after pretreatment (wt %) | 1.8 | 0.163 | 22.39 | 5.19 | 0.106 | 10.56 |

Next, a step of allowing the pretreated phosphate inorganic processing solution to absorb nitric acid was performed. After which, the composition of the phosphate inorganic solution was analyzed by titration. The results are shown in Table 6.

Thereafter, hydrogen and nitrogen were introduced into the phosphate inorganic processing solution at 50° C. under a pressure of 24 kg/cm² in the presence of catalysts. Hydroxylammonium phosphate was obtained. The selectivity for reducing nitrate ions to give hydroxylamine is 90.50%.

TABLE 6

|  | $H^+$ | $H_2PO_4^-$ | $NH_4^+$ | $NH_3OH^+$ | $NO_3^-$ |
|---|---|---|---|---|---|
| Composition of inorganic processing solution after absorbing nitric acid (wt %) | 0.298 | 20.13 | 4.19 | 0.082 | 15.6 |
| Selectivity for hydroxylamine production |  |  | 90.50% |  |  |

Example 4

A phosphate inorganic processing solution in a hydroxylamine-oxime recycling system was used as an acidic buffer solution for preparing hydroxylammonium phosphate. The composition of the phosphate inorganic solution was analyzed by titration. The results are shown in table 7.

Then, 0.023 wt % yellow prussiate of potassium [$K_4Fe(CN)_6$] was added to the phosphate inorganic processing solution and stirred at 25° C. to form precipitate. The precipitate was filtered off, and a pretreated acidic buffer solution was obtained. The composition of the pretreated phosphate inorganic processing solution was analyzed by titration. The results are shown in table 7.

TABLE 7

|  | pH | $H^+$ | $H_2PO_4^-$ | $NH_4^+$ | $NH_3OH^+$ | $NO_3^-$ |
|---|---|---|---|---|---|---|
| Composition of inorganic processing solution before pretreatment (wt %) | 1.8 | 0.163 | 22.39 | 5.12 | 0.103 | 10.34 |
| Composition of inorganic processing solution after pretreatment (wt %) | 1.8 | 0.162 | 22.39 | 5.13 | 0.102 | 10.35 |

Next, a step of allowing the pretreated phosphate inorganic processing solution to absorb nitric acid was performed. After which, the composition of the phosphate inorganic solution was analyzed by titration. The results are shown in Table 8.

Thereafter, hydrogen and nitrogen were introduced into the phosphate inorganic processing solution at 50° C. under a pressure of 24 kg/cm² in the presence of catalysts. Hydroxylammonium phosphate was obtained. The selectivity for reducing nitrate ions to give hydroxylamine is 87.20%.

TABLE 8

|  | $H^+$ | $H_2PO_4^-$ | $NH_4^+$ | $NH_3OH^+$ | $NO_3^-$ |
|---|---|---|---|---|---|
| Composition of inorganic processing solution after absorbing nitric acid (wt %) | 0.292 | 20.13 | 4.17 | 0.082 | 15.7 |
| Selectivity for hydroxylamine production |  |  | 87.20% |  |  |

Example 5

A phosphate inorganic processing solution in a hydroxylamine-oxime recycling system was used as an acidic buffer solution for preparing hydroxylammonium phosphate. The composition of the phosphate inorganic solution was analyzed by titration. The results are shown in table 9.

Then, 0.043 wt % yellow prussiate of sodium [$Na_4Fe(CN)_6$] was added to the phosphate inorganic processing solution and stirred at 35° C. to form precipitate. The precipitate was filtered off, and a pretreated acidic buffer solution was obtained. The composition of the pretreated phosphate inorganic processing solution was analyzed by titration. The results are shown in table 9.

TABLE 9

|  | pH | $H^+$ | $H_2PO_4^-$ | $NH_4^+$ | $NH_3OH^+$ | $NO_3^-$ |
|---|---|---|---|---|---|---|
| Composition of inorganic processing solution before pretreatment (wt %) | 1.8 | 0.164 | 22.32 | 5.15 | 0.108 | 10.43 |
| Composition of inorganic processing solution after pretreatment (wt %) | 1.8 | 0.163 | 22.32 | 5.13 | 0.106 | 10.42 |

Next, a step of allowing the pretreated phosphate inorganic processing solution to absorb nitric acid was performed. After which, the composition of the phosphate inorganic solution was analyzed by titration. The results are shown in Table 10.

Thereafter, hydrogen and nitrogen were introduced into the phosphate inorganic processing solution at 50° C. under a pressure of 24 kg/cm² in the presence of catalysts. Hydroxylammonium phosphate was obtained. The selectivity for reducing nitrate ions to give hydroxylamine is 89.21%.

TABLE 10

|  | $H^+$ | $H_2PO_4^-$ | $NH_4^+$ | $NH_3OH^+$ | $NO_3^-$ |
|---|---|---|---|---|---|
| Composition of inorganic processing solution after absorbing nitric acid (wt %) | 0.297 | 20.13 | 4.14 | 0.078 | 15.25 |
| Selectivity for hydroxylamine production |  |  | 89.21% |  |  |

Example 6

A phosphate inorganic processing solution in a hydroxylamine-oxime recycling system was used as an acidic buffer solution for preparing hydroxylammonium phosphate. The composition of the phosphate inorganic solution was analyzed by titration. The results are shown in table 11.

Then, 0.063 wt % yellow prussiate of sodium [$Na_4Fe(CN)_6$] was added to the phosphate inorganic processing solution and stirred at 45° C. to form precipitate. The precipitate was filtered off, and a pretreated acidic buffer solution was obtained. The composition of the pretreated phosphate inorganic processing solution was analyzed by titration. The results are shown in table 11.

TABLE 11

|  | pH | $H^+$ | $H_2PO_4^-$ | $NH_4^+$ | $NH_3OH^+$ | $NO_3^-$ |
|---|---|---|---|---|---|---|
| Composition of inorganic processing solution before pretreatment (wt %) | 1.8 | 0.158 | 22.42 | 5.12 | 0.108 | 10.37 |
| Composition of inorganic processing solution after pretreatment (wt %) | 1.8 | 0.157 | 22.41 | 5.13 | 0.106 | 10.35 |

Next, a step of allowing the pretreated phosphate inorganic processing solution to absorb nitric acid was performed. After which, the composition of the phosphate inorganic solution was analyzed by titration. The results are shown in Table 12.

Thereafter, hydrogen and nitrogen were introduced into the phosphate inorganic processing solution at 50° C. under the pressure of 24 kg/cm² in the presence of catalysts. Hydroxylammonium phosphate was obtained. The selectivity for reducing nitrate ions to give hydroxylamine is 91.50%.

TABLE 12

|  | $H^+$ | $H_2PO_4^-$ | $NH_4^+$ | $NH_3OH^+$ | $NO_3^-$ |
|---|---|---|---|---|---|
| Composition of inorganic processing solution after absorbing nitric acid (wt %) | 0.295 | 20.13 | 4.15 | 0.082 | 15.8 |
| Selectivity for hydroxylamine production |  |  | 91.50% |  |  |

Example 7

A phosphate inorganic processing solution in a hydroxylamine-oxime recycling system was used as an acidic buffer solution for preparing hydroxylammonium phosphate. The composition of the phosphate inorganic solution was analyzed by titration. The results are shown in table 13.

Then, 0.05 wt % yellow prussiate of ammonium [$(NH_4)_4Fe(CN)_6$] was added to the phosphate inorganic processing solution and stirred at 75° C. to form precipitate. The precipitate was filtered off, and a pretreated acidic buffer solution was obtained. The composition of the pretreated phosphate inorganic processing solution was analyzed by titration. The results are shown in table 13.

TABLE 13

|  | pH | $H^+$ | $H_2PO_4^-$ | $NH_4^+$ | $NH_3OH^+$ | $NO_3^-$ |
|---|---|---|---|---|---|---|
| Composition of inorganic processing solution before pretreatment (wt %) | 1.8 | 0.168 | 22.26 | 5.18 | 0.103 | 10.46 |
| Composition of inorganic processing solution after pretreatment (wt %) | 1.8 | 0.165 | 22.26 | 5.19 | 0.105 | 10.45 |

Next, a step of allowing the pretreated phosphate inorganic processing solution to absorb nitric acid was performed. After which, the composition of the phosphate inorganic solution was analyzed by titration. The results are shown in Table 14.

Thereafter, hydrogen and nitrogen were introduced into the phosphate inorganic processing solution at 50° C. under a pressure of 24 kg/cm² in the presence of catalysts. Hydroxylammonium phosphate was obtained. The selectivity for reducing nitrate ions to give hydroxylamine is 88.50%.

TABLE 14

| | H⁺ | H₂PO₄⁻ | NH₄⁺ | NH₃OH⁺ | NO₃⁻ |
|---|---|---|---|---|---|
| Composition of inorganic processing solution after absorbing nitric acid (wt %) | 0.305 | 20.17 | 4.14 | 0.077 | 16.2 |
| Selectivity for hydroxylamine production | | | 88.50% | | |

Example 8

A phosphate inorganic processing solution in a hydroxylamine-oxime recycling system was used as an acidic buffer solution for preparing hydroxylammonium phosphate. The composition of the phosphate inorganic solution was analyzed by titration. The results are shown in table 15.

Then, 0.095 wt % yellow prussiate of ammonium [(NH₄)₄Fe(CN)₆] was added to the phosphate inorganic processing solution and stirred at 95° C. to form precipitate. The precipitate was filtered off, and a pretreated acidic buffer solution was obtained. The composition of the pretreated phosphate inorganic processing solution was analyzed by titration. The results are shown in table 15.

TABLE 15

| | pH | H⁺ | H₂PO₄⁻ | NH₄⁺ | NH₃OH⁺ | NO₃⁻ |
|---|---|---|---|---|---|---|
| Composition of inorganic processing solution before pretreatment (wt %) | 1.8 | 0.167 | 22.34 | 5.19 | 0.102 | 10.48 |
| Composition of inorganic processing solution after pretreatment (wt %) | 1.8 | 0.165 | 22.32 | 5.18 | 0.102 | 10.46 |

Next, a step of allowing the pretreated phosphate inorganic processing solution to absorb nitric acid was performed. After which, the composition of the phosphate inorganic solution was analyzed by titration. The results are shown in Table 16.

Thereafter, hydrogen and nitrogen were introduced into the phosphate inorganic processing solution at 50° C. under a pressure of 24 kg/cm² in the presence of catalysts. Hydroxylammonium phosphate was obtained. The selectivity for reducing nitrate ions to give hydroxylamine is 91.50%.

TABLE 16

| | H⁺ | H₂PO₄⁻ | NH₄⁺ | NH₃OH⁺ | NO₃⁻ |
|---|---|---|---|---|---|
| Composition of inorganic processing solution after absorbing nitric acid (wt %) | 0.301 | 20.15 | 4.12 | 0.073 | 16.38 |
| Selectivity for hydroxylamine production | | | 91.50% | | |

Example 9

A phosphate inorganic processing solution in a hydroxylamine-oxime recycling system was used as an acidic buffer solution for preparing hydroxylammonium phosphate. The composition of the phosphate inorganic solution was analyzed by titration. The results are shown in table 17.

Then, 0.18 wt % yellow prussiate of ammonium [(NH₄)₄Fe(CN)₆] was added to the phosphate inorganic processing solution and stirred at 115° C. to form precipitate. The precipitate was filtered off and a pretreated acidic buffer solution was obtained. The composition of the pretreated phosphate inorganic processing solution was analyzed by titration. The results are shown in table 17.

TABLE 17

| | pH | H⁺ | H₂PO₄⁻ | NH₄⁺ | NH₃OH⁺ | NO₃⁻ |
|---|---|---|---|---|---|---|
| Composition of inorganic processing solution before pretreatment (wt %) | 1.8 | 0.158 | 22.39 | 5.16 | 0.103 | 10.43 |
| Composition of inorganic processing solution after pretreatment (wt %) | 1.8 | 0.157 | 22.37 | 5.14 | 0.102 | 10.42 |

Next, a step of allowing the pretreated phosphate inorganic processing solution to absorb nitric acid was performed. After which, the composition of the phosphate inorganic solution was analyzed by titration. The results are shown in Table 18.

Thereafter, hydrogen and nitrogen were introduced into the phosphate inorganic processing solution at 50° C. under a pressure of 24 kg/cm² in the presence of catalysts. Hydroxylammonium phosphate was obtained. The selectivity for reducing nitrate ions to give hydroxylamine is 94.20%.

TABLE 18

| | H⁺ | H₂PO₄⁻ | NH₄⁺ | NH₃OH⁺ | NO₃⁻ |
|---|---|---|---|---|---|
| Composition of inorganic processing solution after absorbing nitric acid (wt %) | 0.304 | 20.18 | 4.08 | 0.064 | 16.4 |
| Selectivity for hydroxylamine production | | | 94.20% | | |

Comparative Example 1

A phosphate inorganic processing solution in a hydroxylamine-oxime recycling system was used as an acidic buffer solution for preparing hydroxylammonium phosphate. The composition of the phosphate inorganic solution was analyzed by titration. The results are shown in table 19.

TABLE 19

| | pH | H⁺ | H₂PO₄⁻ | NH₄⁺ | NH₃OH⁺ | NO₃⁻ |
|---|---|---|---|---|---|---|
| Composition of inorganic processing solution before pretreatment (wt %) | 1.8 | 0.168 | 22.35 | 5.12 | 0.108 | 10.42 |

Next, a step of allowing the pretreated phosphate inorganic processing solution to absorb nitric acid was performed. After which, the composition of the phosphate inorganic solution was analyzed by titration. The results are shown in Table 20.

Thereafter, hydrogen and nitrogen were introduced into the phosphate inorganic processing solution at 50° C. under a pressure of 24 kg/cm² in the presence of catalysts. Hydroxylammonium phosphate was obtained. The selectivity for reducing nitrate ions to give hydroxylamine is 84.35%.

TABLE 20

|  | H⁺ | $H_2PO_4^-$ | $NH_4^+$ | $NH_3OH^+$ | $NO_3^-$ |
|---|---|---|---|---|---|
| Composition of inorganic processing solution after absorbing nitric acid (wt %) | 0.295 | 20.13 | 4.14 | 0.074 | 15.24 |
| Selectivity for hydroxylamine production |  |  |  | 84.35% |  |

Referring to the results of the examples and the comparative example, it is found that when the particular precipitant is added into the acidic buffer solution according to the method of the present invention, metal complexes can be formed and removed from the acidic buffer solution at an acidic condition without pH adjustment. Consequently, the selectivity for hydroxylamine production is promoted by about 8 to 10%.

The foregoing detailed descriptions of the embodiments have been discussed for illustrating the features and functions of the present invention and not for limiting the scope of the present invention. Those skilled in the art can easily make any modifications and variations according to the spirit and principle of the present invention. All such modifications and variations are considered to fall within the spirit and scope of the present invention as defined by the claims.

What is claimed is:

1. A method for preparing hydroxylamine, which comprises the steps of:
  (i) pretreating an acidic buffer solution comprising an acidic buffer reagent, nitric acid or nitrates, and metal impurities, the pretreatment of the acidic buffer solution comprising the steps of:
    (a) adding a precipitant represented by formula (I) to the acidic buffer solution, $$[(A)aM(CN)_6 \cdot xH_2O] \qquad (I)$$

wherein A is selected from the group consisting of IA metals and $NH_4$, M is IIIB metals, a is an integer of 3 or 4, x is an integer of 0 to 10, and pH of the acidic buffer solution is less than 3.5,
    (b) reacting the precipitant with the metal impurities in the acidic buffer solution to form metal complexes, and
    (c) removing the metal complexes from the acidic buffer solution; and
  (ii) reducing nitrate ions provided by the nitric acid or nitrates in the acidic buffer solution with hydrogen in the presence of catalysts to give hydroxylamine.

2. The method according to claim 1, wherein M is iron.

3. The method according to claim 1, wherein the step (b) is conducted at a temperature of 25° C. to 120° C.

4. The method according to claim 3, wherein the step (b) is conducted at a temperature of 40° C. to 95° C.

5. The method according to claim 1, wherein the acidic buffer solution is obtained from synthesis of cyclohexanone oxime.

6. The method according to claim 1, further comprising a step of supplementing nitrate ions into the acidic buffer solution before the step (ii) is carried out.

7. The method according to claim 1, wherein the acidic buffer reagent is selected from the group consisting of sulfuric acid, phosphoric acid, and salts thereof.

8. The method according to claim 1, wherein the metal impurities include iron, molybdenum, nickel, bismuth, cobalt, copper, manganese, tin, tungsten, and zinc.

9. The method according to claim 1, wherein the pH of the acidic buffer solution is between 0.5 and 1.8.

* * * * *